US00PP21862P3

(12) United States Plant Patent
Saville

(10) Patent No.: US PP21,862 P3
(45) Date of Patent: Apr. 12, 2011

(54) MINIATURE ROSE PLANT NAMED 'SAVAMONT'

(50) Latin Name: *Rosa chinensis hybrida*
Varietal Denomination: Savamont

(75) Inventor: John M. Saville, Newburyport, MA (US)

(73) Assignee: Nor'East Miniature Roses, Inc., Rowley, MA (US)

( * ) Notice: Subject to any disclaimer, the term of this patent is extended or adjusted under 35 U.S.C. 154(b) by 2386 days.

(21) Appl. No.: 10/015,143

(22) Filed: Dec. 10, 2001

(65) Prior Publication Data

US 2003/0110542 P1 Jun. 12, 2003

(51) Int. Cl.
*A01H 5/00* (2006.01)

(52) U.S. Cl. ..... Plt./122

(58) Field of Classification Search ..... Plt./122
See application file for complete search history.

(56) References Cited

U.S. PATENT DOCUMENTS

PP5,770 P * 7/1986 De Ruiter ..... Plt./122
PP6,517 P * 1/1989 Benardella ..... Plt./116

* cited by examiner

*Primary Examiner* — Bruce R. Campell
*Assistant Examiner* — W C Haas
(74) *Attorney, Agent, or Firm* — Christie, Parker & Hale, LLP

(57) ABSTRACT

A new and distinct Miniature Rose plant having attractive Red flowers.

1 Drawing Sheet

Botanical designation: *Rosa chinensis hybrida.*

BACKGROUND OF THE INVENTION

The present invention relates to a new and distinct variety of *Rosa chinensis hybrida.* The new variety was created by crossing as seed parent the variety known as 'BENALAV' (U.S. Plant Pat. No. 6,517) and as pollen parent, the variety known as 'RUMIRED' (U.S. Plant Pat. No. 5,770). The varietal denomination of the new variety is 'SAVAMONT'.

SUMMARY OF THE INVENTION

Among the novel characteristics possessed by the new variety which distinguishes it from its parents and all other varieties of which I am aware, is its attractive Red flowers.

Asexual reproduction by propagation of vegetative cuttings of the new variety as performed in Essex County, Mass. show that the foregoing and other distinguishing characteristics come true to form and are established and transmitted through succeeding propagation.

COMPARISON WITH PARENTS

The new variety may be distinguished from its parents in flower color. The new variety is much taller and more upright than its pollen parent 'RUIMIRED' and whereas the flower of the new variety is more Blue Red in color, flower of 'RUIMIRED' is more of an Orange Red color. The new variety differs from its seed parent BENLAV in flower color. Flowers of BENLAV are lavender pink and flowers of the new variety are red.

BRIEF DESCRIPTION OF ILLUSTRATION

The accompanying photograph illustrates a typical specimen of the new variety and shows the flowering thereof from bud to full bloom depicted in color as nearly true as it is reasonably possible to make in a color illustration of the character. Throughout this specification, color references and/or values are based upon The Royal Horticultural Society Colour Chart and terminology used in the color descriptions herein refers to plate numbers in this color chart except where common terms of color definition are employed.

DESCRIPTION OF THE NEW VARIETY

The following observations were made of 5 year-old plants of the new variety grown in 2-gallon plastic containers in Essex County, Mass. during the months of July and August. Phenotypic expression may vary with environmental, cultural and climatic conditions, as well as differences in conditions of light and soil.

FLOWER

Blooming habit: Continuous; flowers last about a week on the plant and then drop off cleanly with the peduncle.

*Bud.*—Medium; length about ½ to ⅝ inch just before sepals divide; diameter is approximately ½ inch in width. Form: Obovate. Color: When sepals first divide color near 60A; when petals begin to unfurl, color near 60A.

*Sepals.*—Lanceolate with occasional flags; extending about ⅝ inch beyond tip of bud. Color: Upper Surface: Near 144A. Under surface: Near 147C.

*Peduncle.*—Length: About 1 to 1½ inches. Aspect: Straight. Strength: Erect. Color: Near 144A; texture smooth.

BLOOM

Size: Average size of flower when fully expanded about 1⅞ inches in diameter.

Borne: Clusters of 2 to 8 and also singly.
Form: Opens flat becoming and remaining loosely rolled outward.
Petalage: Between 24 to 30.
Fragrance: Slight.
Persistence: Flower drops off cleanly.
Lasting quality: Between 7 to 10 days as cut flower.

PETALS

Texture: Smooth.
Appearance: Inside velvety; outside satiny with slightly raised veins.
Form: Broad, spatulate.
Size: Length about 11/16 inch at point of attachment to tip; outer petal width about 3/4 inch.
Arrangement: Shingle-like; regularly arranged.
Color:
*During first 2 days.*—Petals at center of flower upper side near 46A, under side near 53A; outer petals upper side near 46A, under side near 60A.
In full bloom.—Inner petals upper side between 60A and 53A, underside near 53A; outer petals upper side near 53A, under side near 60A.
*Base of petals (point of attachment).*—White.
*General tonality from a distance.*—Dark Red.
*Color change.*—Very slight as bloom ages. General tonality from a distance: Dark Red even after 3 or more days.
*Petaloids in center.*—About 2 to 6; usually about 1/8 to 2/8 inches wide and 9/32 to 11/32 inches long; shape is obovate with acuminate base; apex tends toward obtuse but often the outer margin appears malformed being emarginate to varying degrees.
*Color.*—Same as inner petals.
*Texture.*—Smooth.

REPRODUCTIVE ORGANS

Arrangement of stamens:
Filaments and anthers: Regularly arranged around styles.
Stamens: About 100 or more.
Filaments: About 1/16 to 1/8 inch; color Deep Yellow near 20A.
Anthers: Near 20B.
Pollen: Ample quantity; color near 17A.
Pistils: About 30.
Styles: Thin, uneven length between 1/16 to 3/16 inch; color near 53C.
Stigmas: Near 27B.
Receptacle:
*Shape.*—Round; surface texture pubescent.
*Size.*—About 5/16 inch.
*Color.*—Off-White near 196D.
Hips:
*Shape.*—Mostly globular, occasionally apple and pear shaped.
*Size.*—Average diameter at widest point between 13/16 and 14/16 inch.
*Color.*—Some areas near 28B; some areas near 167A.
*Seeds.*—Seeds do not protrude; surface texture glabrous; color near 19C; seeds appear to be viable; number of seeds per hip is variable and unknown; size and shape of seeds also unknown.

PLANT

Form: Upright, compact.
Growth: Vigorous, uniform branching.
Size: At maturity, height between 18 to 21 inches; width between 20 to 24 inches.
Foliage: Generally 5 leaflets, occasionally 3 or 7 leaflets.
*Size.*—About 3½ inches from stem to tip measured along the rachis; about 1¾ inches on mature leaflet at terminal leaflet base to tip.
*Quantity.*—Abundant.
*Color.*—New foliage: Upper side near 146A flushed with 187A; under side near 146B flushed with 187A. Mature foliage: Upper side near 147A; under side near 147B.
*Shape.*—Oval pointed; shape of the base of the leaflets is rounded and the apex is acute.
*Texture.*—Upper side: Semi-glossy and glabrous. Under side: Matte and glabrous.
*Edge.*—Serrated.
*Serration.*—Fine on new foliage becoming somewhat coarse and slightly uneven on older foliage.
Stipules: Very finely bearded; length is about ½ the length to the first set of leaflets; upper surface color near 147B, under surface near 146C.
Rachis: Smooth texture; upper side color near 147A, under side near 144A.
*Prickles.*—Occasional; between 2 to 3 prickles on mature leaves, occasionally 5; color near 144C.
Resistance to disease: Good resistence to insects and Mildew; average resistence to Blackspot, resistence to Rust not observed.

WOOD

New shoots:
*Bark.*—Smooth.
*Wood.*—Near 144A.
Old wood:
*Bark.*—Smooth.
*Wood.*—Near 146A.
Flowering stem: Length between 4½ to 5½ inches.
Thorns:
*Quantity.*—About 4 per inch on main stalks from base; about 6 to 8 per inch on laterals from stalk; fewer closest to bud/flower.
*Form.*—Flat base, slightly curved downward to a point; irregularly positioned.
*Length.*—About ¼ inch.
*Color.*—Immature thorns: Tip near 161C, at the base near 183D. Mature thorns: Near 165B.
*Prickles.*—None on main stalks.
Winter hardiness: Tested hardy zones 4 to 9; winter protection recommended in Zones 5 and colder.

I claim:

1. A new and distinct Miniature Rose plant of the variety substantially as shown and described.

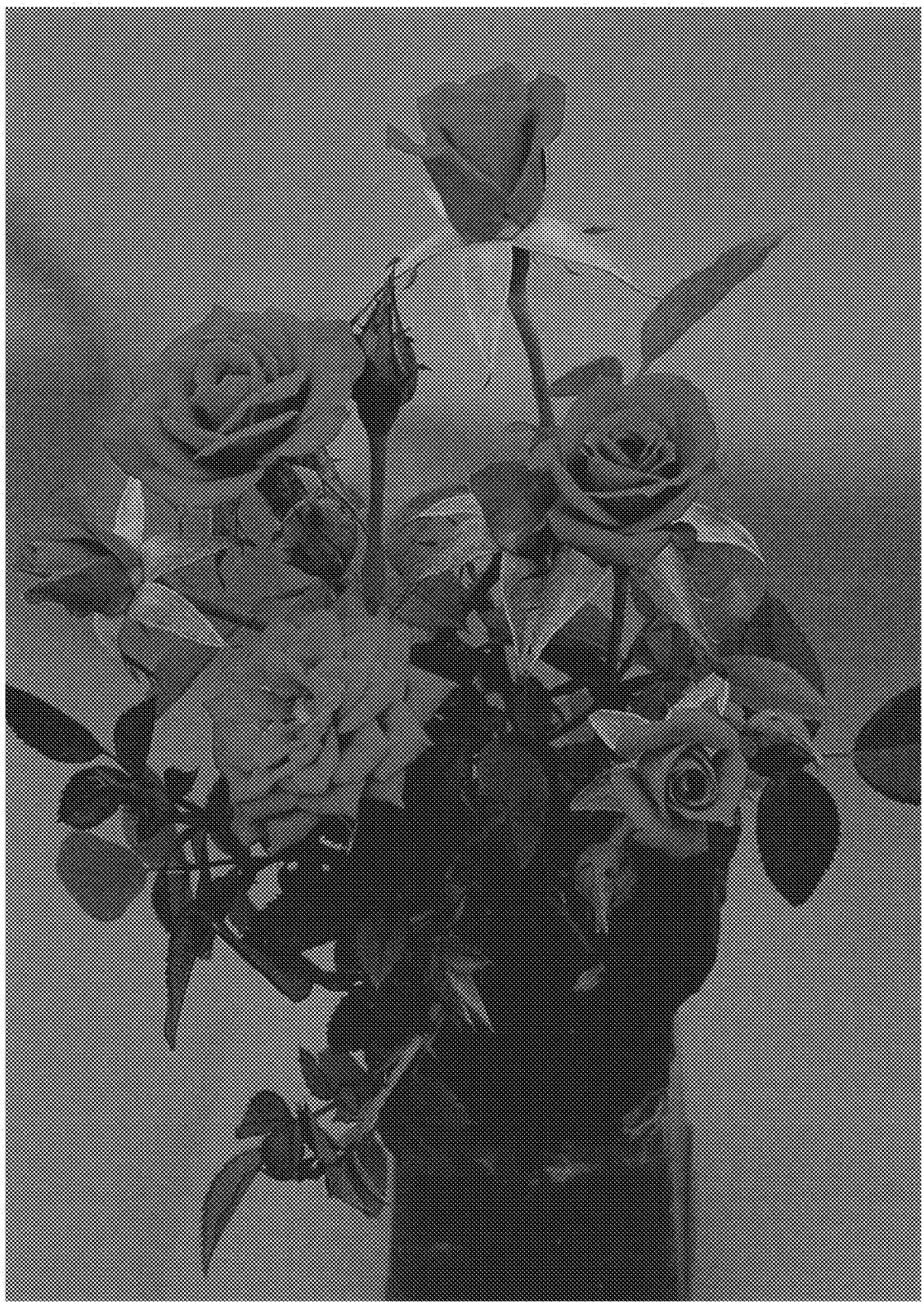

* * * * *